(12) United States Patent
Kaiser et al.

(10) Patent No.: US 7,651,660 B2
(45) Date of Patent: Jan. 26, 2010

(54) APPARATUS FOR IRRADIATING LIQUIDS

(75) Inventors: Klaus Kaiser, Köln (DE); Jörg Kauling, Köln (DE); Hans-Jürgen Henzler, Solingen (DE); Isabell Günther, Leverkusen (DE); Franz Schmitt, Bergisch Gladbach (DE); Erhard Beckers, Burscheid (DE); Stefan Quest, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1774 days.

(21) Appl. No.: 10/011,141

(22) Filed: Nov. 12, 2001

(65) Prior Publication Data

US 2002/0096648 A1 Jul. 25, 2002

(30) Foreign Application Priority Data

Nov. 13, 2000 (DE) ................................ 100 56 096

(51) Int. Cl.
| | |
|---|---|
| B08B 17/00 | (2006.01) |
| A61L 2/00 | (2006.01) |
| B01J 19/08 | (2006.01) |
| G01N 23/00 | (2006.01) |
| B01D 63/00 | (2006.01) |
| B01D 17/06 | (2006.01) |
| C12M 1/02 | (2006.01) |

(52) U.S. Cl. ............... 422/24; 422/1; 422/6; 422/186; 422/44; 422/905; 250/432 R; 250/455.11; 210/748; 210/319; 210/320; 210/512.3; 210/321.63; 435/302.1

(58) Field of Classification Search .............. 422/1, 422/6, 24, 186, 44, 905; 250/432 R, 455.11; 210/748, 319, 320, 512.3, 321.63; 435/302.1
See application file for complete search history.

(56) References Cited

U.S. PATENT DOCUMENTS 1,151,267 A * 8/1915 Helbronner ................. 422/24

(Continued)

FOREIGN PATENT DOCUMENTS

DE          43 04 444 A1  *  8/1994

(Continued)

OTHER PUBLICATIONS

Merriam-Webster Online internet printout, definition of "vane" and Dictionary.com internet printout, definition of "vane".*

(Continued)

*Primary Examiner*—Jill Warden
*Assistant Examiner*—Monzer R Chorbaji
(74) *Attorney, Agent, or Firm*—Norris McLaughlin & Marcus, P.A.

(57) ABSTRACT

Described is a reactor for irradiating ultraviolet light into a fluid reaction medium (3). The reactor consists of at least one housing (15) which encloses a tubular cavity, with a radiation source (1) for generating ultraviolet light and an inner tube (2) which, together with the housing (15), forms an irradiation chamber (26) which, in particular, is of annular shape, the irradiation chamber (26) being connected at least with an inlet (13) and an outlet (14) for the reaction medium (3) and is perfused by reaction medium (3) in the longitudinal direction of the tube (2), the irradiation chamber (26) being equipped with means (6, 25) for generating an additional radial flow routing of the reaction medium (3).

22 Claims, 10 Drawing Sheets

U.S. PATENT DOCUMENTS

| | | | | |
|---|---|---|---|---|
| 2,636,991 | A | 4/1953 | Postell | 250/47 |
| 3,434,804 | A * | 3/1969 | Winn | 422/135 |
| 3,438,743 | A * | 4/1969 | Steijner et al. | 422/111 |
| 3,572,651 | A * | 3/1971 | Harker | 366/185 |
| 3,708,410 | A * | 1/1973 | Platz et al. | 422/186 |
| 3,904,363 | A * | 9/1975 | Free | 250/431 |
| 4,274,970 | A * | 6/1981 | Beitzel | 210/748 |
| 4,769,131 | A * | 9/1988 | Noll et al. | 210/85 |
| 5,433,738 | A * | 7/1995 | Stinson | 607/92 |
| 5,466,425 | A * | 11/1995 | Adams | 422/186.3 |
| 5,679,249 | A * | 10/1997 | Fendya et al. | 210/321.63 |
| 5,785,845 | A | 7/1998 | Colaiano | 210/167 |
| 6,375,833 | B1 * | 4/2002 | Marston et al. | 210/85 |
| 6,570,167 | B1 * | 5/2003 | Bryer et al. | 250/431 |
| 6,596,230 | B1 * | 7/2003 | Woo et al. | 422/22 |

FOREIGN PATENT DOCUMENTS

| | | |
|---|---|---|
| DE | 43 39 006 A1 | 5/1995 |
| DE | 197 19 645 A1 | 11/1997 |
| EP | 0 202 820 * | 11/1986 |
| EP | 0 202 820 A2 | 11/1986 |
| EP | 0 202 891 A2 | 11/1986 |
| EP | 0 803 472 A1 | 10/1997 |
| GB | 1 448 411 * | 9/1976 |
| GB | 1448411 * | 9/1976 |
| GB | 0 202 820 * | 11/1986 |
| GB | EP 0 202 820 A2 * | 11/1986 |

OTHER PUBLICATIONS

"Symposium-In-Print Virucidal Treatment of Blood Protein Products with UVC Radiation", Photochemistry and Photobiology, 1997, 65(3): 432-435.

* cited by examiner

APPARATUS FOR IRRADIATING LIQUIDS

The invention relates to a reactor for irradiating ultraviolet light into a fluid reaction medium. The reactor consists of at least one housing which encloses a tubular cavity, with a radiation source for generating ultraviolet light and an inner tube which, together with the housing, forms an irradiation chamber which, in particular, is of annular shape, the irradiation chamber being connected at least with an inlet and an outlet for the reaction medium and is perfused by reaction medium in the longitudinal direction of the tube, the irradiation chamber being equipped with means for generating an additional radial flow routing of the reaction medium.

BACKGROUND OF THE INVENTION

The sterilization of liquid media is an essential precondition when employing production methods in the field of biotechnology and food technology. The objective is reliable and complete depletion of microorganisms and/or viruses hand in hand with virtually complete preservation of valuable substances. Sterilization is applied both to the feed stock (e.g. nutrient media for fermentations) and end products (e.g. milk products or pharmaceutical active proteins). For the food industry, the sterilization techniques are used, inter alia, with a view to longer shelf life, whereas their use in the pharmaceutical industry is regulated by strict quality assurance requirements. For example, the use of pharmaceutical products of human or animal origin requires a number of virus deactivation steps which are based on different principles of action and must each ensure viral depletion by at least four powers of ten. The need to ensure "viral safety" of course also applies to pharmaceuticals produced by genetic engineering methods.

One of the viral depletion methods proposed in the literature as having minimal impact on the product is the irradiation with ultraviolet light. The treatment of plasma and blood products with UV light is known in principle. As early as during the second world war, large quantities of plasma were collected and irradiated with UV light. The UV treatment of blood derivatives is of particular interest, however, with respect to non-enveloped, heat-resistant viruses. Chin et al (Chin, S., Jin, R., Wang, X. L., Hamman, J., Gerard Marx, Xlaode Mou, Inger Andersson, Lars-Olof Lindquist, and Bernhard Horowitz (1997). Virucidal Treatment of Blood Protein Products with UVC Radiation. Photochemistry and Photobiology 65(3): 432-435) were able to show that a treatment of plasma products with UV light results in deactivation of hepatitis A and parvoviruses.

UV irradiation is aimed at mutagenic changes in the genetic material of the microorganisms or viruses which, above a minimum radiation dose, lose their ability to reproduce. It is an object of the invention to develop for this purpose a reliable and optimally effective apparatus for irradiation with UV light.

Problems in the use of reactors for radiating ultraviolet light into liquid reaction media are caused by the fact that the radiation intensity in the medium to be treated decreases exponentially with increasing distance from the radiation source. Microorganisms and viruses at a greater distance from the radiation source are therefore destroyed more slowly or even not at all. Because of this effect, which is magnified considerably as the optical absorptance of the medium increases, very large irradiation surface areas are employed in the prior art, as found e.g. in thin-film reactors. The thin-film reactors currently in use can be scaled up only with difficulty to industrial scales, as the only way to keep the film thickness constant in the scale-up is to increase the diameter in proportion with the throughput, which on an industrial scale results in infeasibly large reactors. A further negative factor is the unfavourable residence time behaviour of the liquid films, which given the generally low penetration depth of the UV radiation to the reaction medium are necessarily very thin and consequently exhibit laminar flow, in which any transfer transverse to the principal flow direction is absent by definition. The layers close to the wall remain for considerably longer times, because of the velocity profile dropping linearly to zero towards the wall, than the layers further away from the wall. In order to achieve the minimum radiation dose necessary for destruction even in the more rapidly flowing liquid layer far from the wall, the mean residence time of the film has to be increased. This, however, leads to an increased radiation exposure and consequently to greater damage to the products.

Also known and described are so-called annular-gap reactors. A UV annular-gap reactor of conventional design consists of a tubular metal housing set into which is a quartz tube containing a rod-shaped UV radiation source, thereby forming an annular-gap chamber. In this reactor type, the reaction medium flows through the annular chamber only in an axial direction, which likewise is not advantageous with a view to good mass transfer—a similar situation as with the thin-film reactors.

The disadvantages described of the reactor types should be capable of being overcome by more favourable flow routing which, in addition to a narrow residence time spectrum, also permit good transfer in the liquid perpendicular to the principal flow direction. Proposals for this purpose include tangential-inflow annular gap reactors From EP 803 472 A1 e.g. is a reactor for radiating ultraviolet light into a reaction medium, comprising an annular chamber as the irradiation zone, in which the design of the inlet is such that the reaction medium enters the annular chamber tangentially.

The performance of a reactor with tangential inflow has marginal advantages, compared with a "classic" annular-gap reactor. Process engineering studies show that wall friction causes the tangential flow profile to be transformed into an axial profile very soon after the inlet. The Dean vortices, which are theoretically postulated at least for the region of tangential cross flow and by means of which the cross-transfer of the reaction medium within the annular gap is to be intensified, are not present according to visual studies and CFD studies (flow simulation), which means that tangential-inflow annular-gap reactors of this type do permit some improvement in the mixing behaviour, but still do not allow complete exchange. The secondary flow and the concomitant improved mass transfer is therefore restricted to the zones near the inlet.

It was possible to demonstrate that this behaviour can be tolerated in the treatment of weakly absorbing reaction media (e.g. water treatment), as mixing is adequate for this purpose and the UV dose can be increased to circumvent this drawback. For applications in connection with the treatment of protein solutions this appeared impossible, as the proteins would suffer irreversible damage in the process.

It is therefore novel and surprising that the reactors of the type mentioned at the outset are also suitable for treating virus-contaminated protein solutions if the radiation chamber over its entire length includes means for additional radial flow routing of the reaction medium and in particular if, relative to the diameter of the housing, a specific reactor length is not exceeded. The proposed L/D ratios should preferably be less than 100.

As made clear by the above description, it is an object of the invention to provide apparatuses of the type mentioned at the outset having an optimized, more uniform mixing behaviour for the reaction medium.

SUMMARY OF THE INVENTION

The invention relates to a reactor for radiating ultraviolet light into a fluid reaction medium, comprising a housing which encloses a tubular cavity, with a radiation source for generating ultraviolet light and an inner tube which, together with the housing, forms an irradiation chamber which, in particular, is of annular shape, the irradiation chamber being connected at least with an inlet and an outlet for the reaction medium and is perfused by reaction medium in the longitudinal direction of the tube, characterized in that the irradiation chamber is equipped with means for generating an additional radial flow routing of the reaction medium.

The apparatus (reactor) for radiating UV light into liquids is distinguished, because of its optimal and uniform mixing behaviour, by improved mass transfer, thereby ensuring reliable and effective sterilization. The apparatus is readily integrated into existing plants and is easy to clean. Another advantage is the compact design of the apparatus.

DETAILED DESCRIPTION

The apparatus is characterized in that specific flow conditions are generated, in an annular-gap duct transparent to UV light, which cause intensive mass transfer over the entire length of the duct. The apparatus comprises e.g. a UV radiation source, which can be encompassed by a quartz field tube (emitter jacket tube), and a product duct (irradiation chamber) which is transparent to UV light and is perfused by the reaction medium. The particular characteristic of the irradiation chamber is intensive, uniform cross-mixing prevailing over the entire length and perpendicular to the principal direction of the product flow, and a residence time distribution constrained by turbulent product flow.

Said cross-mixing ensures that the liquid layers which are at a greater distance from the radiation source and which, particularly with strongly light-absorbing media, receive little or no UV radiation, enter into intensive transfer with the UV irradiated layers close to the radiation source. This is ensured e.g. by special flow routing in the apparatus, producing a multiplicity of successive quasi-cellular circulation flows. The requisite residence time of the products in the reactive duct layers is thus minimized, resulting in minimal damage to the products due to the radiation dose in conjunction with reliable sterilization or virus deactivation. The secondary flows are generated by agitation, upon flow round internals or upon flow through spiral ducts.

In a preferred type of construction, the design of the reactor is such that the radiation source is disposed in the inner tube and the inner tube is transparent to the ultraviolet light.

The inner wall of the housing in this context particularly preferably has a coating comprising a material which reflects UV radiation.

In an alternative preferred type of construction, the radiation source of the reactor is disposed outside the housing and the housing is transparent to the ultraviolet light.

In that case, the wall of the inner tube particularly preferably has a coating comprising a material which reflects UV radiation.

A preferred means of generating additional radial flow routing of the reaction medium is a cylindrical stirrer, especially a cylinder stirrer having from 2 to 10 stirrer blades, which is disposed in the irradiation chamber.

The continuous-flow reactors equipped with an agitator which are preferentially to be used for gentle UV treatment effect cross-mixing by advantageously utilizing the resulting radial and Taylor flows and combinations of these. Taylor vortices are produced in rotating-cylinder stirred reactors as a result of the inner cylinder being driven. If an internally driven cylinder stirrer is used, which for reasons of precise rotary movement should advantageously be fabricated from metallic materials, the UV irradiation can also take place through the static external quartz glass jacket round which the UV tubes are positioned. This apparatus requires numerous UV radiation sources and consequently is more complicated to operate. Furthermore, only that fraction of the total amount of UV radiation available can be utilized with virtually no loss which is absorbed at right angles to the glass wall, whereas the radiation into the other irradiation directions is considerably attenuated owing to the fractions of light. In the case of centric irradiation through an inner cylinder tightly enclosing the UV radiation source these drawbacks are eliminated. On constructional grounds (these include, inter alia, problems with providing a satisfactory seal, in terms of sterility, between the rotating inner cylinder and the tank, and with contact-free mounting of the UV radiation source), however, a driven inner glass cylinder, required to generate the Taylor vortices, cannot be achieved except at the expense of the complex design.

A considerably simpler solution for building up an internally driven tangential flow is provided by a cylinder stirrer which preferably has from 2 to 10 stirrer blades and rotates around the inner cylinder with a small wall spacing of preferably from 0.2 to 20 mm. The stirrer blades having a width of preferably from 0.5 to 30 mm can be carved from a thin-walled precision tube, e.g. by means of cavern-like incisions.

CFD studies have shown, surprisingly, that the optional fitting of additional baffles on the outer cylinder periphery, which cause tangential flow to be attenuated in favour of radial flows for the purpose of further improvement in the cross transfer, does not adversely effect the residence time behaviour. The stirrer is driven via an external motor with a slide ring-sealed stirrer shaft or preferably packinglessly by means of an electromagnetically coupled drive mechanism or an impeller driven by the incoming product stream. Mechanically intensified cleaning of the reactors can take place in a simple manner in the closed state with the stirrer drive mechanism switched on, or by brushing after the inner glass cylinder has been removed.

The U.S. Pat. No. 5,433,738 discloses an irradiation reactor for irradiating water which includes a helical conduit having a circular cross section. Said reactor does not, however, exhibit adequate cross mixing, e.g. as required for virus deactivation, which means that its use for virus deactivation is too unreliable.

With the below-described, preferred, continuous-flow annular-gap reactors fitted with static internals, moving elements can be entirely dispensed with. With these, cross-mixing can be effected by Dean vortices, free jets and product redistribution. Dean vortices occur in spiral pipe flows or duct flows. It has now been found that the use of spiral tubes whose flanks have a cross section flattened towards the radiation source, e.g. using rectangular or D-shaped profiles, are to be preferred compared with the round cross sections known from the prior art, to avoid attenuation of the injected UV light by light being reflected.

Preference is therefore given to an embodiment of the reactor in which the means for producing additional radial flow routing of the reaction medium and the irradiation chamber is formed by a helical tube which is transparent to UV radiation and has a flattened cross section.

Particularly preferably, the cross section of the helical tube preferably has rounded corners and is rectangular, oval or half-round.

The use of this type of reactors comprising a helical tube is essentially limited, however, to clean liquids without extreme quality requirements, as the helical tubes are inaccessible or not readily accessible for mechanical cleaning.

Preferentially, spiral type flows can also be produced by spiral passages being carved from one of two cylinders which can be telescoped together in close contact.

The invention preferably therefore also relates to a reactor which is characterized in that the means for producing additional radial flow routing of the reaction medium is formed by one or more, particularly helical ducts which are disposed circumferentially on the inner wall and/or the outer wall, preferably the outer wall of the irradiation chamber.

Particularly preferably, the cross-sectional profile of the ducts preferably has rounded corners and is rectangular, trapezoidal or half-round.

In particular, the ducts have a depth of from 1 to 100 mm, preferably from 2 to 50 mm, and a mean width of from 1 to 200 mm, preferably from 2 to 50 mm, in the cross-sectional profile.

Most especially preferred is a type of construction of a reactor in which the ducts are of helical design and have a pitch of from 3 to 30° (pitch angle), preferably from 8 to 20°.

In the described variant of the reactor comprising an agitator and further comprising the ducts, the irradiation chamber is of open construction over its full length in the direction of the tube axis of the inner tube.

As irradiation is preferentially effected through the inner cylinder, the helical recess is carved from the outer cylinder with an incision depth of preferably from 1 to 40 mm.

Spiral pipe flows can also be produced by means of specially shaped hoses which, according to the invention, are pulled over a cylinder. Preference is therefore also given to a reactor in which the outer wall of the irradiation chamber, and the ducts, are formed by a corrugated hose.

Effecting a perfect seal of the inner flank of the spiral against the glass wall is possible, but not necessarily desirable, if fouling in the low-flow gores around the contact zones between hose (outer cylinder) and quartz glass is to be avoided. Ensuring a minimum gap between flank and glass wall, to form a small annular gap, the spacing advantageously being in the range between 0.1 and 0.8 mm, induces a slip flow which, as a free jet, enters the helical passage located above it where, superimposed by the Dean vortices, it makes an additional contribution to the intensification of the cross-mixing. An advantageous gap between hose (outer cylinder) and glass tube, given a width of the helical duct of from 2 to 20 mm, is from 0.1 to 1 mm, in particular.

In the case of reactors with only axial flow through them, the Dean vortices induced by the spiral pipe flow are entirely dispensed with. Instead, particularly preferably, additional internals are employed to form annular-gap chambers, from about 10 to 100 mm high, having an inner width of preferably from 3 to 15 mm and a height of from 2 to 6 times the width, whose top and bottom boundaries, based on the chamber depths, have a gap spacing of preferably from 5 to 40% with respect to the inner glass cylinder. The product stream, as it passes the boundaries, is accelerated in a gap flow to a higher velocity. This product stream introduced into the next chamber as a free jet aspirates surrounding liquid at the inlet and accelerates it while its own velocity is reduced. A powerful secondary vortex is thus induced. When the free jet exits at the inner glass cylinder, this results in back wash in the outer region of the annular gap. If the disc is sealed against the glass cylinder and an inlet gap is opened at the outer radius of the annular gap, the back wash zone is located near the inner cylinder. With an alternate arrangement of the inlet gaps on the inner and outer radius of the annular gap it is therefore possible not only to generate the vortex, but also multiple alternating redistribution of the product from the inside to the outside and vice versa.

In a possible construction of the reactor, the design of the inlet is such that the reaction medium enters the irradiation chamber tangentially, radially or axially. For radial introduction of the reaction medium, the inlet is to be on the radius of the bottom can, for axial introduction the inlet is to be parallel to the axis of the irradiation chamber. The design with a tangential inlet is employed with particular preference, especially in the type of construction where the irradiation zone is open over its entire length.

In a preferred variant of the reactor, at least one UV sensor comprising a measuring device for measuring the UV intensity of the radiation source is disposed on the reactor, especially in the top or bottom region of the reactor, e.g. near the inlet and/or the outlet.

A further preferred variant of the reactor includes at least one UV sensor comprising a measuring device for measuring the UV intensity in the irradiation chamber, especially in the top or bottom region of the reactor, e.g. near the inlet and/or the outlet of the reactor.

Use of the reactor is directed towards a multiplicity of different applications for the UV irradiation and/or sterilization of liquids.

The invention further relates to the use of the reactor according to the invention for irradiating and sterilizing fluid media and especially liquids containing microorganisms and/or viruses, preferably foodstuffs, particularly preferably milk products or fruit juice products or drinking water, chemical or pharmaceutical products, especially preferably virus vaccines, active substances or proteins produced by genetic engineering, e.g. active substances or proteins from transgenic animals or plants, blood plasma or products produced from blood plasma.

BRIEF DESCRIPTION OF THE DRAWINGS

The following provides a more detailed explanation of specific embodiments of the invention with reference to figures, in which.

EXAMPLES

Example 1

Figure 1:
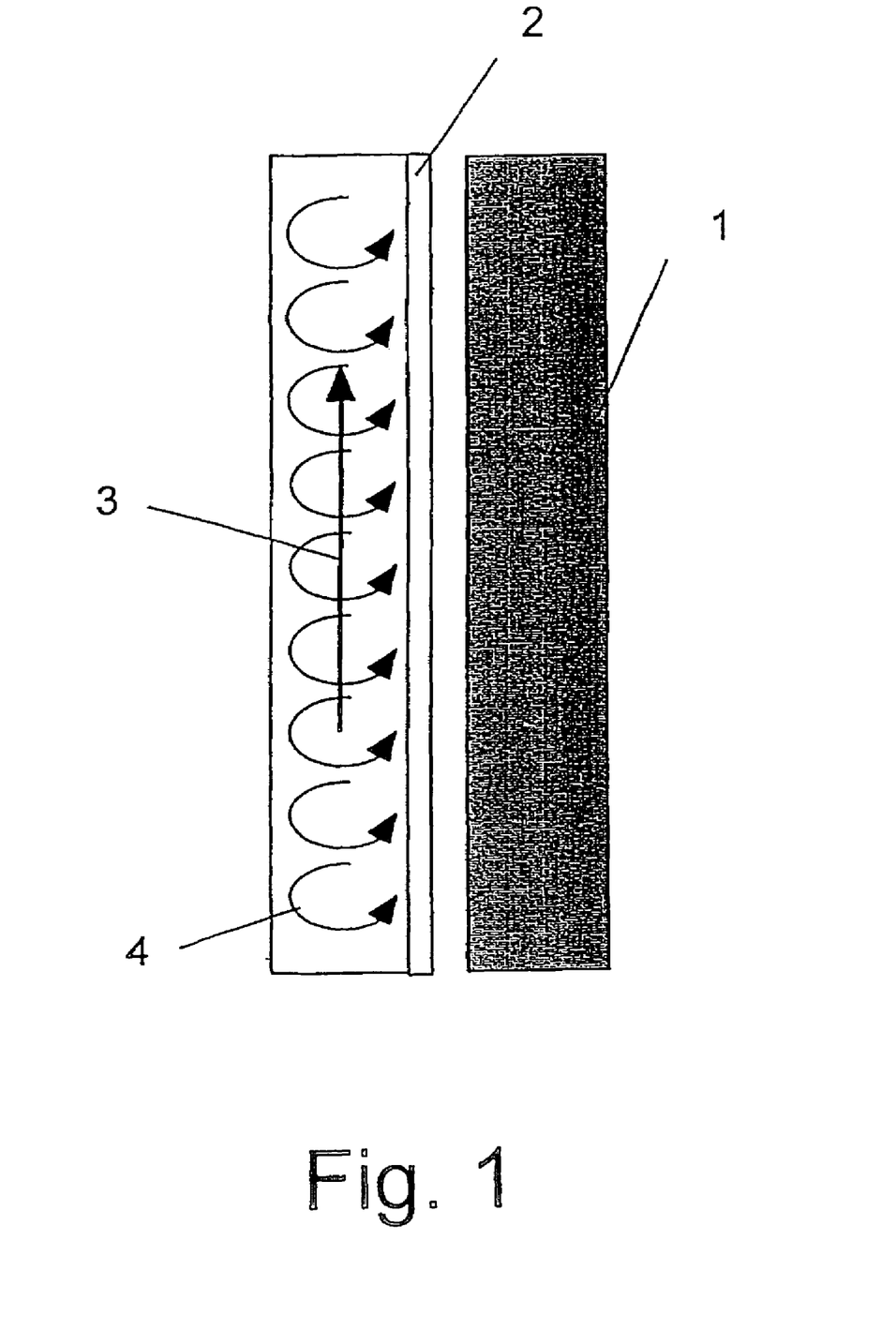
FIG. 1 shows a schematic section through part of an irradiation chamber.
Figures 2, 2A:
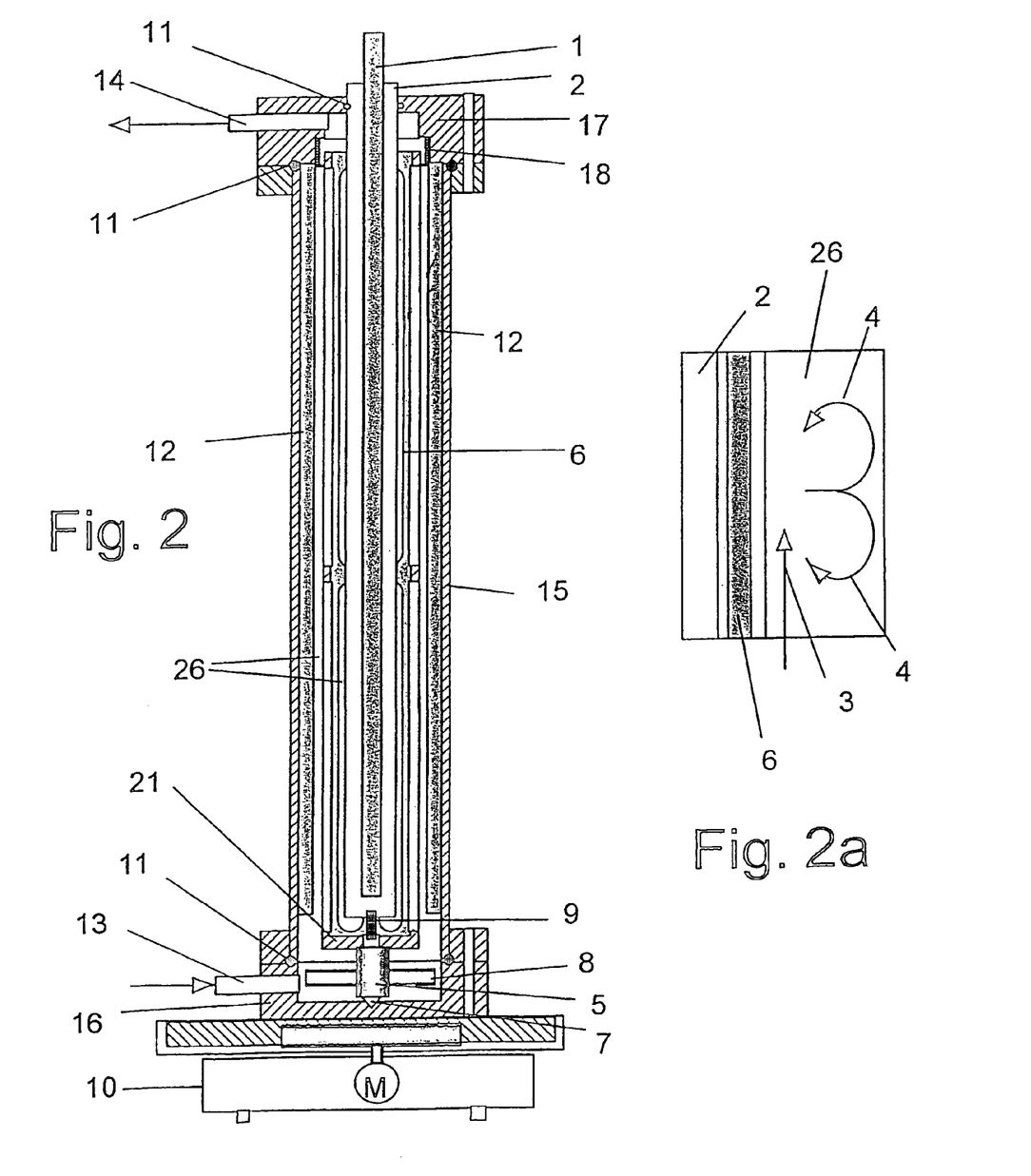
FIG. 2 shows an annular-gap stirred reactor comprising an anchor agitator, centric UV irradiation and magnetic drive in longitudinal section.
FIG. 2a shows an enlarged detail from FIG. 2.

The UV reactor according to FIG. 2 and FIG. 2a consists of a centrically fitted UV lamp 1 (Hg fluorescent tube) having an outer diameter of 25 mm and a length of 850 mm which can be inserted and removed, without coming into contact with product, through a quartz glass jacket 2 (inner quartz glass tube) which is open at the top and has an inner diameter of 26 mm. A seal ensuring the required sterility is provided at the open side of the tube 2 by an O-ring 11 in the top cap 17. Rotating about the glass tube 2, with a small spacing of 0.5 mm, is an anchor agitator 6 fitted with eight stirrer blades. This is supported in the top cap 17 by a sleeve bearing 18 and in the bottom cap 16 on a centring point 7. It is driven via a magnetic clutch, the power provided by an external magnetic stirrer 10 being transmitted contactlessly and consequently without making use of seals to a counter magnet 8 mounted transversely to the stirrer shaft 5. To ensure the wall spacing between anchor agitator 6 and glass tube 2, the axially symmetric position of the tube 2 is ensured by means of a centring pin 9 which is guided within the shaft 5. The annular gap 26 (irradiation chamber) of 5 mm, in which the inactivation reaction takes place, is bounded on the inside by the outer wall of the tube 2 and on the outside by the inner wall, optionally fitted with four baffles 12 having a width of 3 mm, of the jacket tube 15 which has flanges welded on at both ends to secure the bottom 16 and top cap 17.

The product is delivered to the spout 13 of the bottom cap at a flow rate of 150-300 l/h and is drawn off at the top cap 17 via a spout 14.

Figure 3:
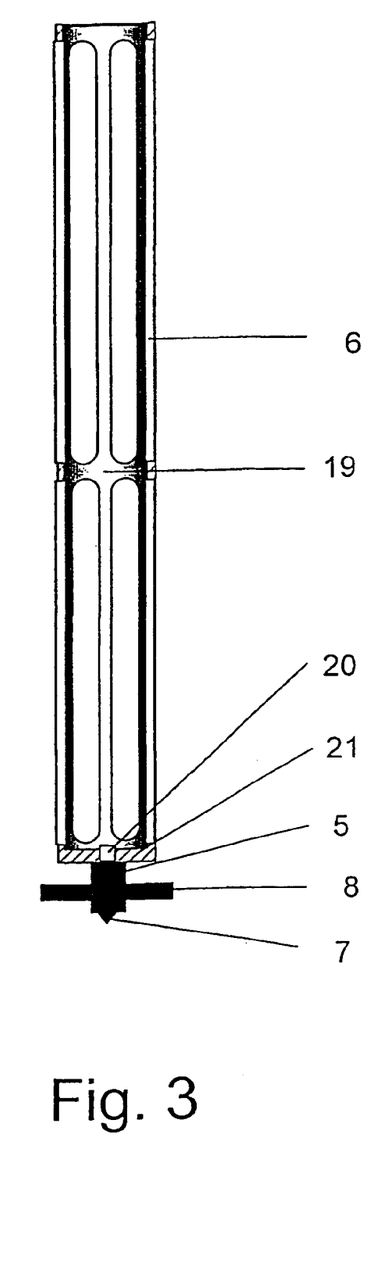
FIG. 3 shows an anchor agitator, carved out in the manner of a cavern, from FIG. 2 with a magnet.

The cylinder stirrer 6 carrying eight blades of the shape according to FIG. 3 is fabricated from a precision tube having an outer diameter 31 mm and a wall thickness of 0.8 mm by cutting out 16 cavern-like recesses. For reasons of stability, the recesses do not run continuously across the entire stirrer length, but extend as far as the connecting fins 19. Via a disc 21, the cylinder stirrer 6 is linked to the stirrer shaft 5. The centring hole 20 which extends right into the shaft 5, is used to centre the tube 2 close to the bottom. The stirrer is centred in turn in the bottom cap 16 via a centring point 7.

Example 2

Figure 4:
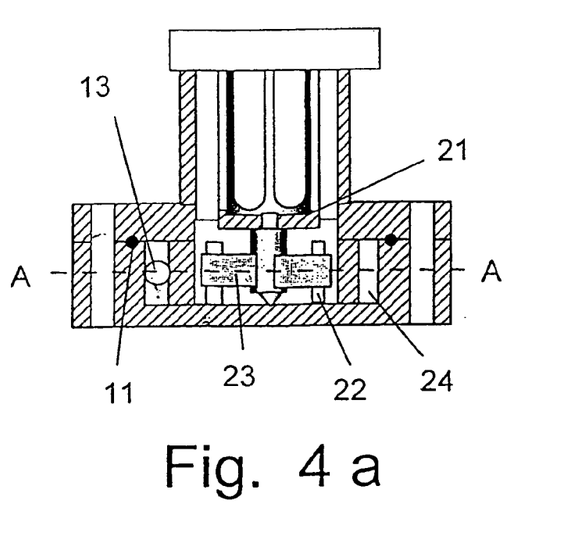
FIG. 4a shows an impeller drive for the anchor agitator according to FIG. 2 in longitudinal section B-B
FIG. 4b shows the impeller drive according to FIG. 4a in cross section A-A

The impeller drive which is used as an alternative to the magnetic clutch in the design according to FIG. 2 and likewise does not make use of seals, for the anchor agitator 6 according to FIG. 4a (section B-B) and 4b (section A-A) consists of four convexly curved impellers 23 which are fastened to the stirrer shaft 5 and have a height of 10 mm. The diameter of the impeller is 39 mm. It is driven by the product which is injected tangentially into an upstream annular chamber 24 and is directed onto the side vanes via four slits 22 which are tangentially oriented with respect to the inner chamber and each have a slit width of 0.8 mm.

Example 3

Figures 5, 5A:
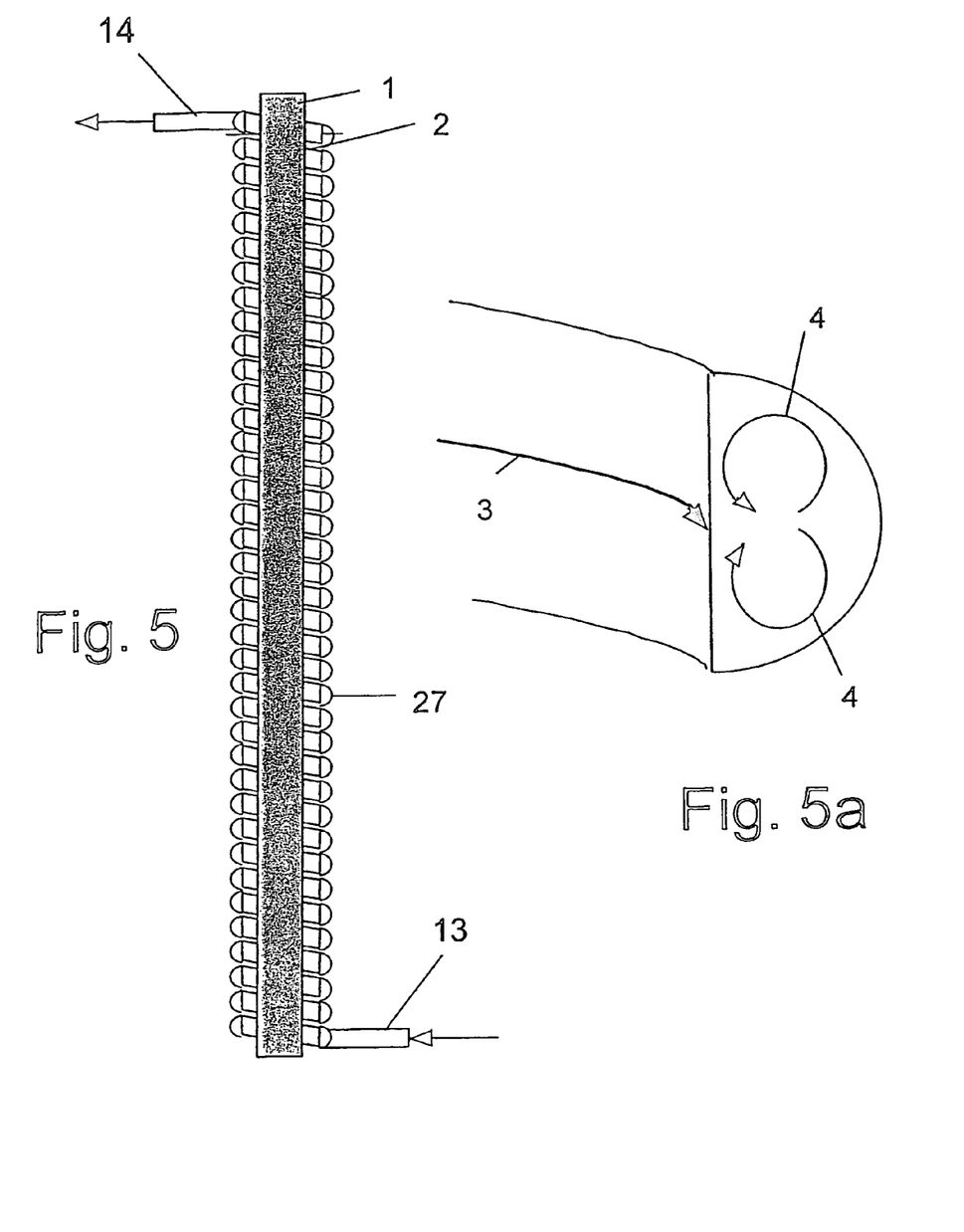
FIG. 5 shows a helical-tube reactor with a half-round tube cross section.
FIG. 5a shows an enlarged detail from FIG. 5.
Figures 6, 6A:
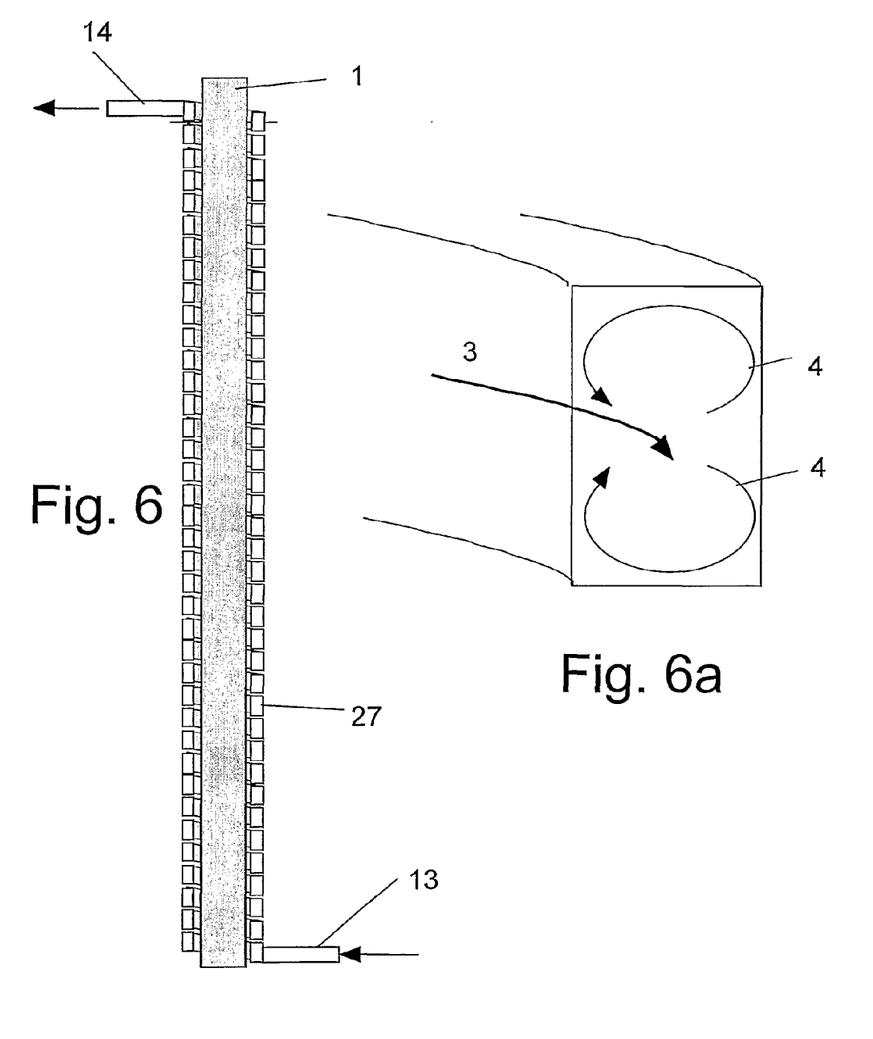
FIG. 6 shows a helical-tube reactor with a rectangular tube cross section.
FIG. 6a shows an enlarged detail from FIG. 6

The UV reactor according to FIG. 5 and FIG. 5a consists of a UV lamp 1 having a diameter of 25 mm, around which a quartz glass tube 27 having a half-round cross section of a diameter of 8 mm and a radius of 4 mm is coiled a small distance away. The UV reactor according to FIG. 6 and FIG. 6a consists of a UV lamp 1 having a diameter of 25 mm, around which a quartz glass tube 27 having a rectangular cross section of a width of 8 mm and a depth of 4 mm is coiled a small distance away. At right angles to the spiral flow 3, secondary vortices 4, so-called Dean vortices are induced which cause the material to be irradiated to be recirculated in the tube 27.

Example 4

Figures 7, 7A:
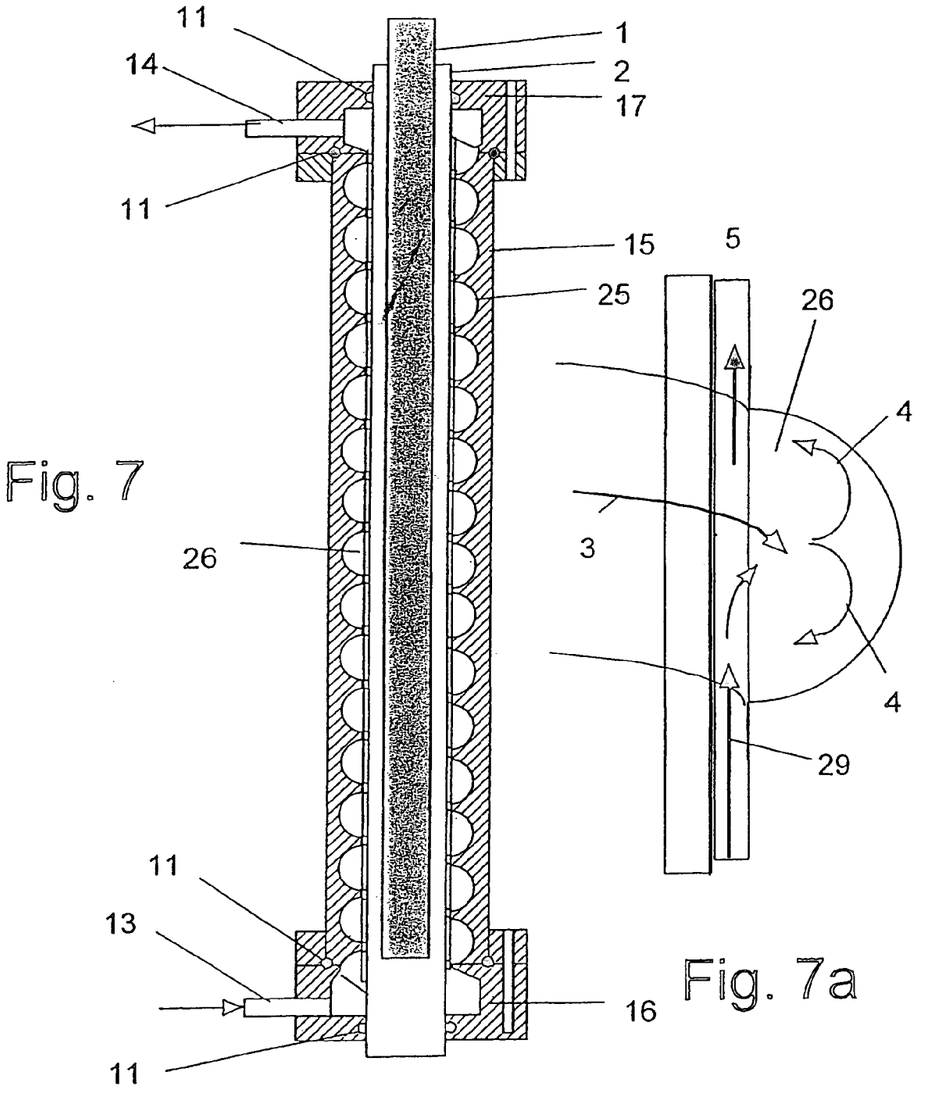
FIG. 7 shows a disassembleable, ducted spiral-tube reactor in longitudinal section.
FIG. 7a shows an enlarged detail from FIG. 6

The UV reactor according to FIG. 7 and FIG. 7a consists of a UV radiation source 1 surrounded by a continuous quartz glass tube 2 which at the top 17 and bottom cap 16 is sealed against the reaction chamber 26 by means of O-rings 11 and which on the outside has product flowing over it in a spiral flow. The contour of the spiral flow is defined by the duct 25 in the outer cylinder 15. To produce a duct 25, a knuckle thread passage is incised into the outer cylinder 15 to a depth of 4 mm and a width of 6 mm. The minimum spacing between glass tube 2 and cylinder is 0.5 mm. This gap allows part of the product flow to enter has a free jet 29 into the flow duct situated above it, in order to reduce fouling problems. The free jet flow 29 directed almost perpendicularly onto the spiral principal flow 3 (see FIG. 7a) results in further amplification of the first one of the two secondary vortices 4 generated by the spiral flow. This arrangement ensures significantly improved uniform irradiation of the product, compared with the helical tube.

Example 5

Figures 8, 8A:
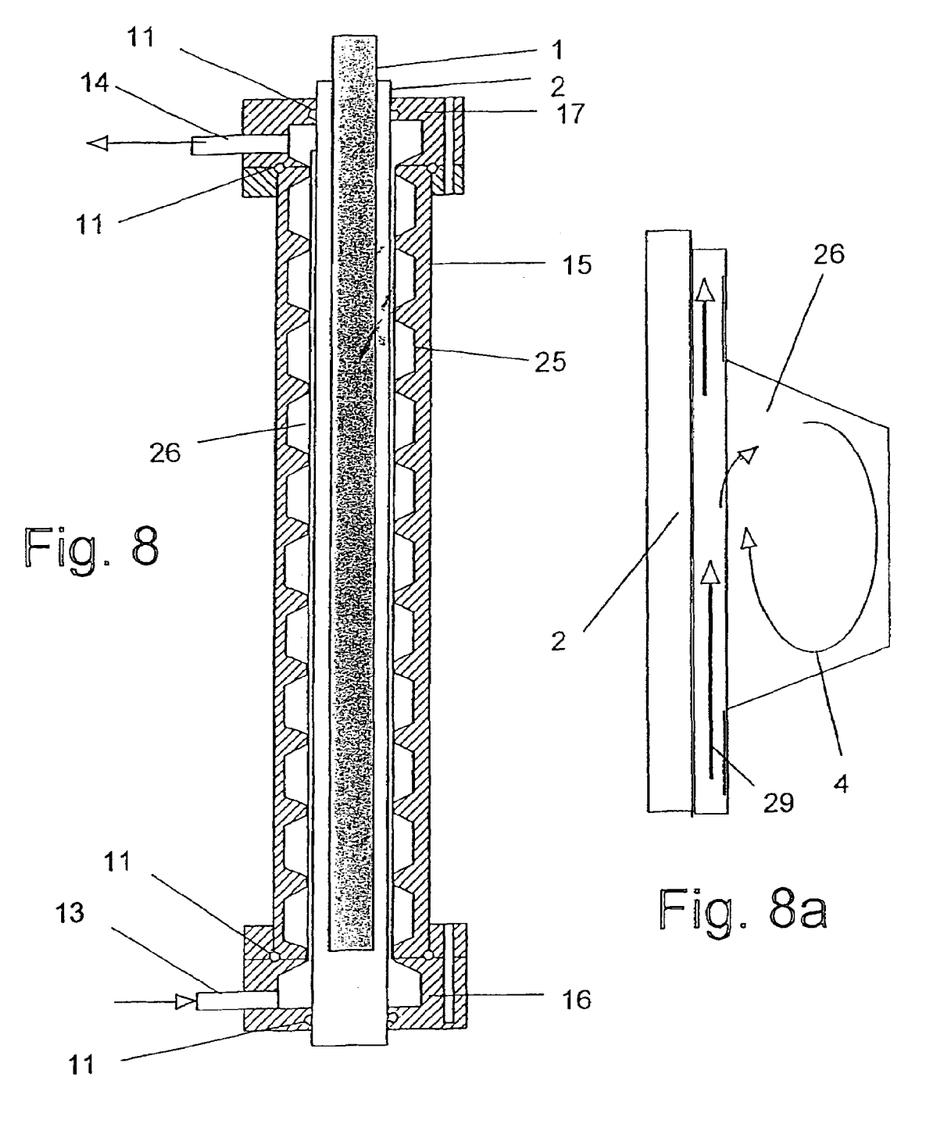
FIG. 8 shows a free-jet reactor driven at the inner diameter of the annular gap and having trapezoidal ducts, in longitudinal section
FIG. 8a shows an enlarged detail from FIG. 8.

The UV reactor according to FIG. 8 and FIG. 8a consists of a UV radiation source 1 surrounded by a continuous quartz glass tube 2 which at the top 17 and bottom cap 16 is sealed against the reaction chamber 26 by means of O-rings 11 and which has axial flow over it on the product side. The sawtooth-shaped contour of the ducts 25' of the outer cylinder 15 creates a multiplicity of disjunct annular-gap chambers having a height of 30 mm and a gap width of 4 mm for the secondary vortices 4 to form (compare FIG. 8a). The secondary vortices are driven by free jets 29 which are generated in the annular gap having a width of 0.7 mm as the product stream enters the ducts 25'.

Example 6

Figures 9, 9A:
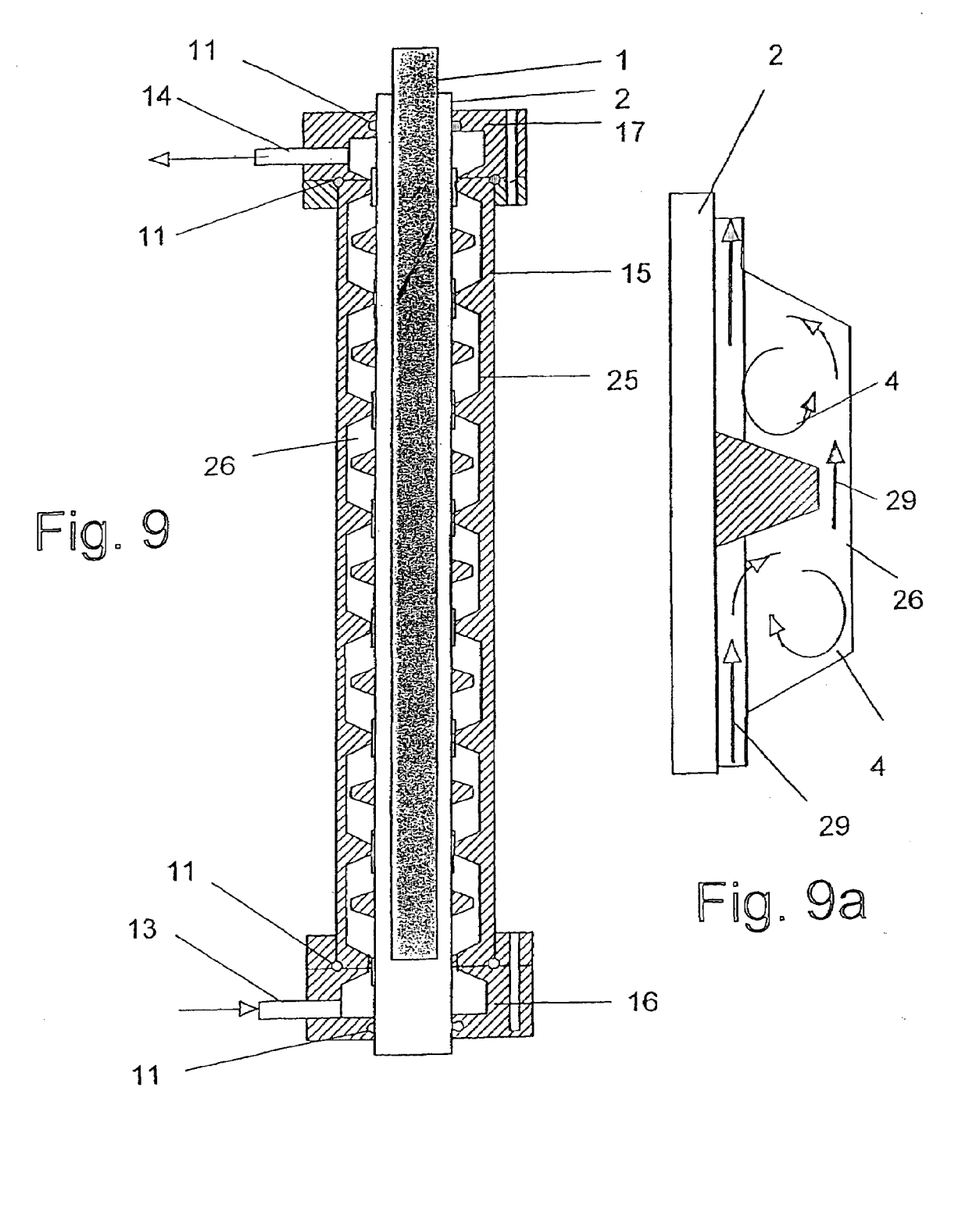
FIG. 9 shows a redistribution reactor with alternating product feed at the inner and outer diameter of the annular gap.
FIG. 9a shows an enlarged detail from FIG. 9.

The UV reactor according to FIG. 9 and FIG. 9a consists of a UV radiation source 1 surrounded by a continuous quartz glass tube 2 which at the top 17 and bottom cap 16 is sealed against the reaction chamber 26 by means of O-rings 11 and which has axial flow over it on the product side. As a result of the special contour of the ducts 25' of the outer cylinder, chambers having a width of 4 mm and a height of 30 mm are formed in which countercurrent secondary vortices 4 driven by free jets 61 are generated which result in alternating redistribution of the product from the inside to the outside of the chambers. The axial free jets are generated in annular gaps having a width of 0.7 mm on the inner and outer circumference of the chambers.

Example 7

Figure 10:
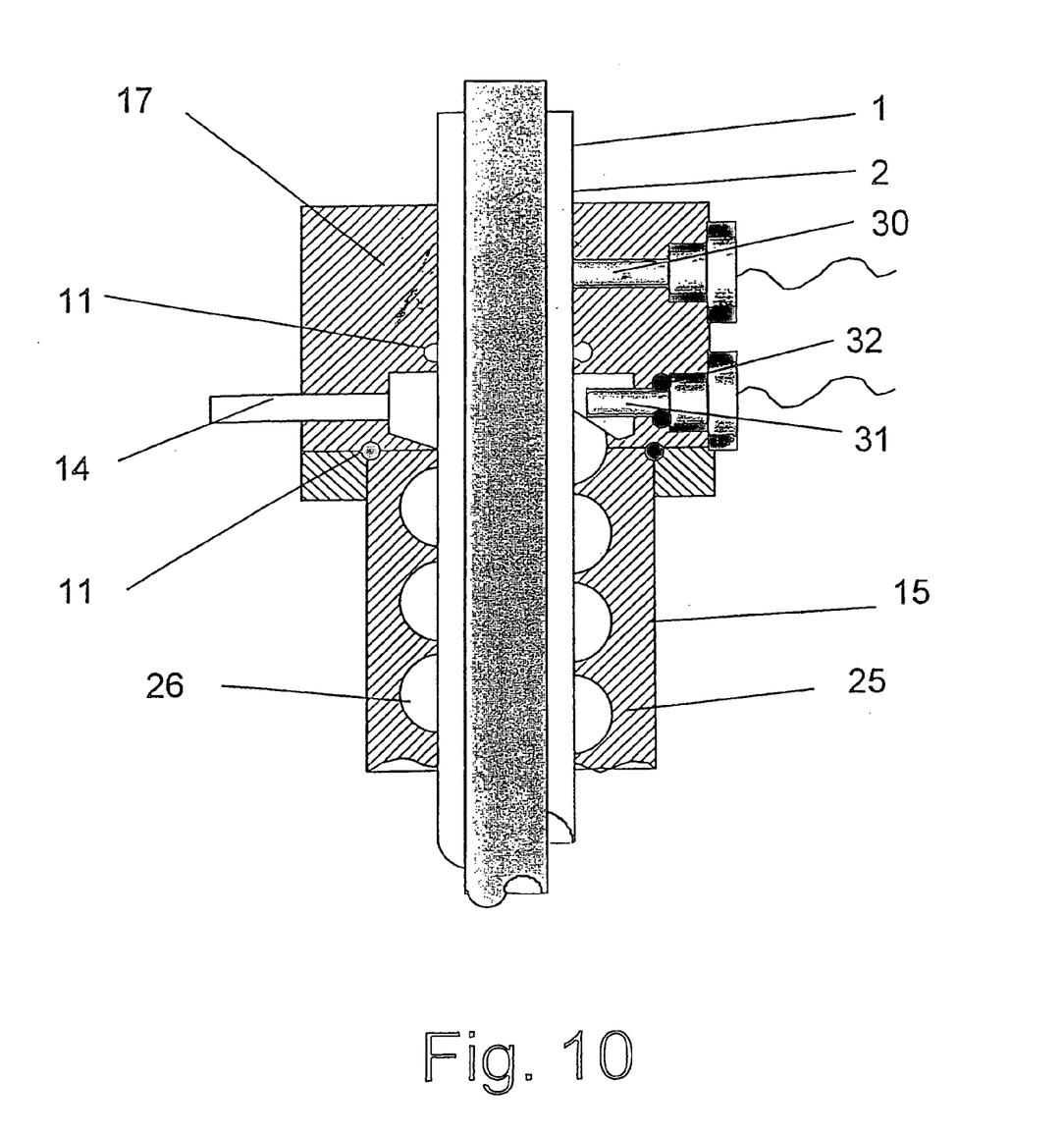
FIG. 10 shows the top section of an annular-gap reactor with UV sensors.
Figure 11:
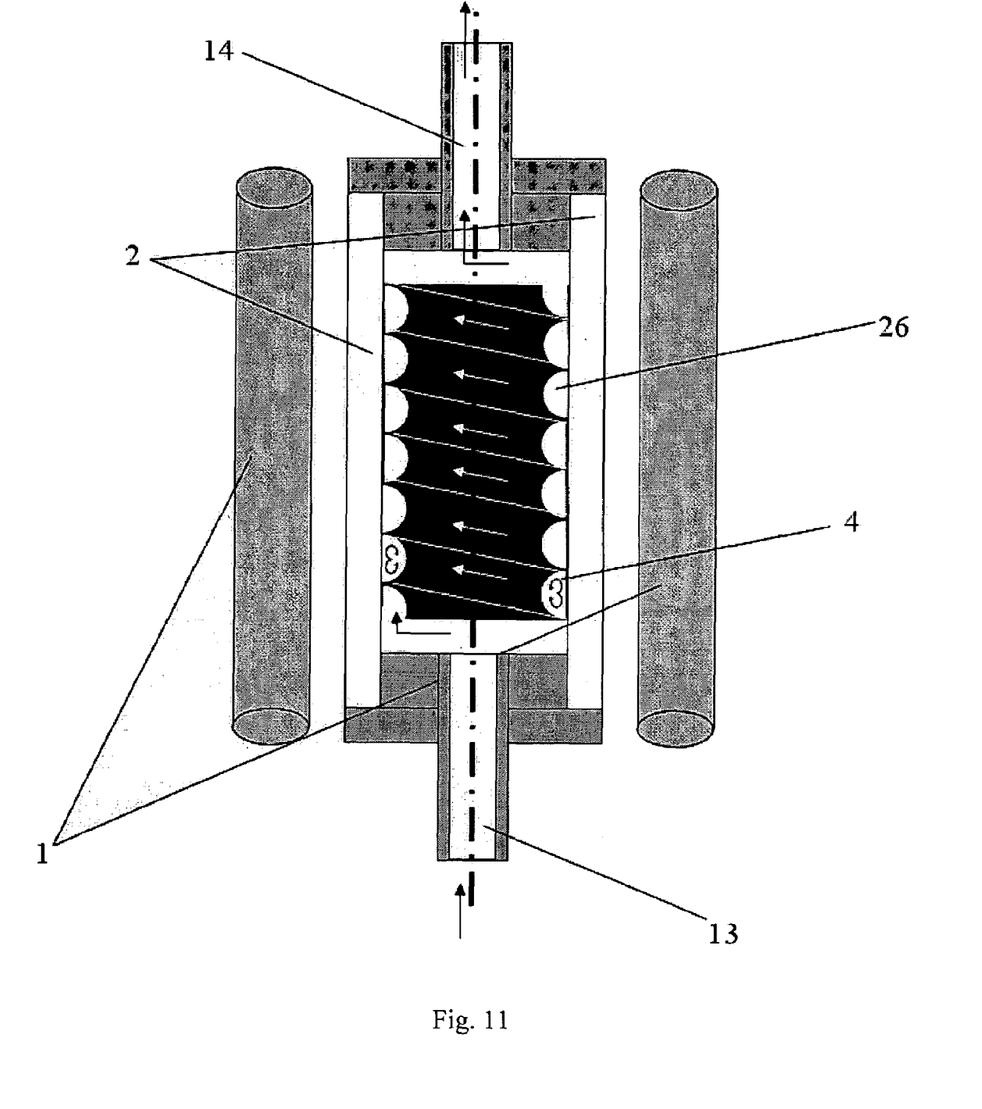
FIG. 11 illustrates the reactor of the invention having a reaction chamber 26, an outer quartz glass jacket 2', secondary vortices 4, inlet 13, outlet 14 and a radiation source (lamp) 1 disposed outside the housing.

The UV reactor according to FIG. 10 (partial view) is modified, compared with the reactor according to FIG. 7, in that the gap between glass tube 2 and outer cylinder 15 is omitted.

Additionally fitted in the top region 17 is a UV sensor 30 which directly measures the UV radiation emitted by the UV radiation source 1. This e.g. allows the UV intensity to be controlled.

A second UV sensor 31 is arranged in the irradiation chamber in order to allow "fouling processes" to be observed in the reactor.

At the bottom end of the reactor, two further UV sensors are present for purposes which are in principle identical to those mentioned above (not shown in FIG. 10).

The invention claimed is:

1. Reactor for radiating ultraviolet light into a fluid reaction medium, comprising a housing which encloses a tubular cavity, with a radiation source for generating ultraviolet light and an inner tube which, together with the housing, forms an irradiation chamber which is of annular shape, the irradiation chamber being connected with an inlet and an outlet for the reaction medium and is perfused by reaction medium in the longitudinal direction of the tube, wherein the irradiation chamber is equipped with a vortex generating element selected from the group consisting of a UV transparent helical tube having a flattened cross section as said irradiation chamber, a rotatable cylindrical stirrer within said irradiation chamber, and helical ducts disposed circumferentially on the inner wall, the outer wall, or both of the irradiation chamber, wherein the cross-sectional profile of the ducts is rectangular, trapezoidal or half-round.

2. Reactor according to claim 1, wherein the radiation source is disposed in the inner tube and the inner tube is transparent to the ultraviolet light.

3. Reactor according to claim 2, wherein the inner wall of the housing has a coating comprising a material which reflects UV radiation.

4. Reactor according to claim 1, wherein the radiation source is disposed outside the housing and the housing is transparent to the ultraviolet light.

5. Reactor according to claim 4, wherein the wall of the inner tube has a coating comprising a material which reflects UV radiation.

6. Reactor according to claim 1, wherein said vortex generating element is a UV transparent helical tube, having a flattened cross section, as said irradiation chamber.

7. Reactor according to claim 6, wherein the cross section of the helical tube is rectangular, oval, half-round or trapezoidal.

8. Reactor according to claim 1, wherein said vortex generating element is a rotatable cylindrical stirrer.

9. Reactor according to claim 1, wherein said vortex generating element is one or more helical ducts which are disposed circumferentially on the inner wall, the outer wall or both, of the irradiation chamber.

10. Reactor according to claim 9, wherein the cross-sectional profile of the ducts is rectangular, trapezoidal or half-round.

11. Reactor according to claim 9 wherein the ducts have a depth of from 1 to 100 mm and a mean width of from 1 to 200 mm in the cross-sectional profile.

12. Reactor according to claim 9, wherein the ducts are of helical design and have a pitch of from 3 to 30°.

13. Reactor according to claim 9, wherein the irradiation chamber is of open construction over its full length in the direction of the tube axis of the inner tube.

14. Reactor according to claim 9, wherein the outer wall of the irradiation chamber, and the ducts, are formed by a corrugated hose.

15. Reactor according to claim 9, wherein baffles are disposed on the wall of the irradiation chamber.

16. Reactor according to claim 1, wherein the design of the inlet is such that the reaction medium enters the irradiation chamber tangentially.

17. Reactor according to claim 16, wherein the ratio of the length of the reactor to the diameter of the housing is limited to L/D<100.

18. Reactor according to claim 1, wherein the design of the inlet is such that the reaction medium enters the irradiation chamber radially.

19. Reactor according to claim 1, wherein the design of the inlet is such that the reaction medium enters the irradiation chamber axially.

20. Reactor according to claim 1, wherein at least one UV sensor comprising a measuring device for measuring the UV intensity of the radiation source is disposed on the reactor.

21. Reactor according to claim 1, wherein at least one UV sensor comprising a measuring device for measuring the UV intensity in the irradiation chamber is fitted in the top or bottom region of the reactor.

22. Method for irradiating and sterilizing fluid media which comprises irradiating and sterilizing said fluid media with the reactor of claim 1.

* * * * *